United States Patent
Sanders Acedo et al.

(10) Patent No.: US 11,857,675 B2
(45) Date of Patent: *Jan. 2, 2024

(54) METHOD FOR REDUCING THE INCIDENCE AND PREVALENCE OF HUMAN PAPILLOMA VIRUS (HPV) AND FOR PROVIDING PROTECTION AGAINST SEXUALLY TRANSMITTED INFECTIONS

(71) Applicants: Eleonora Sanders Esparza, Cuidad (MX); Barbara Sanders Esparza, Cuidad (MX)

(72) Inventors: Guillermo Sanders Acedo, Colonia Popotia Distrito Federal (MX); Eleonora Sanders Esparza, Cuidad (MX); Barbara Sanders Esparza, Cuidad (MX)

(73) Assignees: Barbara Sanders Esparza, Cuidad de Mexico (MX); Eleonora Sanders Esparza, Cuidad de Mexico (MX); Gina Patricia Sanders Esparza, Cuidad de Mexico (MX); Beatriz Sanders Esparza, Cuidad de Mexico (MX); Claudia Fabiola Sanders Esparza, Cuidad de Mexico (MX); Maria Fernanda Sanders Esparza, Cuidad de Mexico (MX); Olivia Andrea Sanders Esparza, Cuidad de Mexico (MX); Guillermo Sanders Castro, Cuidad de Mexico (MX); Eduardo Sanders Perez, Cuidad de Mexico (MX)

( * ) Notice: Subject to any disclaimer, the term of this patent is extended or adjusted under 35 U.S.C. 154(b) by 447 days.

This patent is subject to a terminal disclaimer.

(21) Appl. No.: 16/921,360

(22) Filed: Jul. 6, 2020

(65) Prior Publication Data
US 2020/0345627 A1  Nov. 5, 2020

Related U.S. Application Data

(63) Continuation-in-part of application No. 15/100,900, filed as application No. PCT/MX2015/000121 on Aug. 27, 2015, now Pat. No. 10,702,470.

(51) Int. Cl.
*A61K 9/34* (2006.01)
*A61K 9/00* (2006.01)
(Continued)

(52) U.S. Cl.
CPC ............ *A61K 9/0039* (2013.01); *A61F 6/144* (2013.01); *A61K 33/34* (2013.01)

(58) Field of Classification Search
CPC .................................................. A61K 9/0039
See application file for complete search history.

(56) References Cited

U.S. PATENT DOCUMENTS

| | | |
|---|---|---|
| 4,005,707 A | 2/1977 | Moulding, Jr. |
| 4,724,832 A | 2/1988 | Strubel et al. |

FOREIGN PATENT DOCUMENTS

WO     2010086681 A1     8/2010

*Primary Examiner* — Benjamin J Packard
(74) *Attorney, Agent, or Firm* — Ryan T. Grace; Advent, LLP

(57) ABSTRACT

Methods comprising the insertion of a uterine cervical device into the lower part of the uterine cavity and endocervix for decreasing the incidence of the human papillomavirus in women, mainly types 16 and 18, thus preventing the development of uterine cervical cancer; for modifying the cervical microbiota; for increasing leukocytes and protecting against sexually transmitted infections in women.

19 Claims, 1 Drawing Sheet

(51) Int. Cl.
*A61F 6/14* (2006.01)
*A61K 33/34* (2006.01)

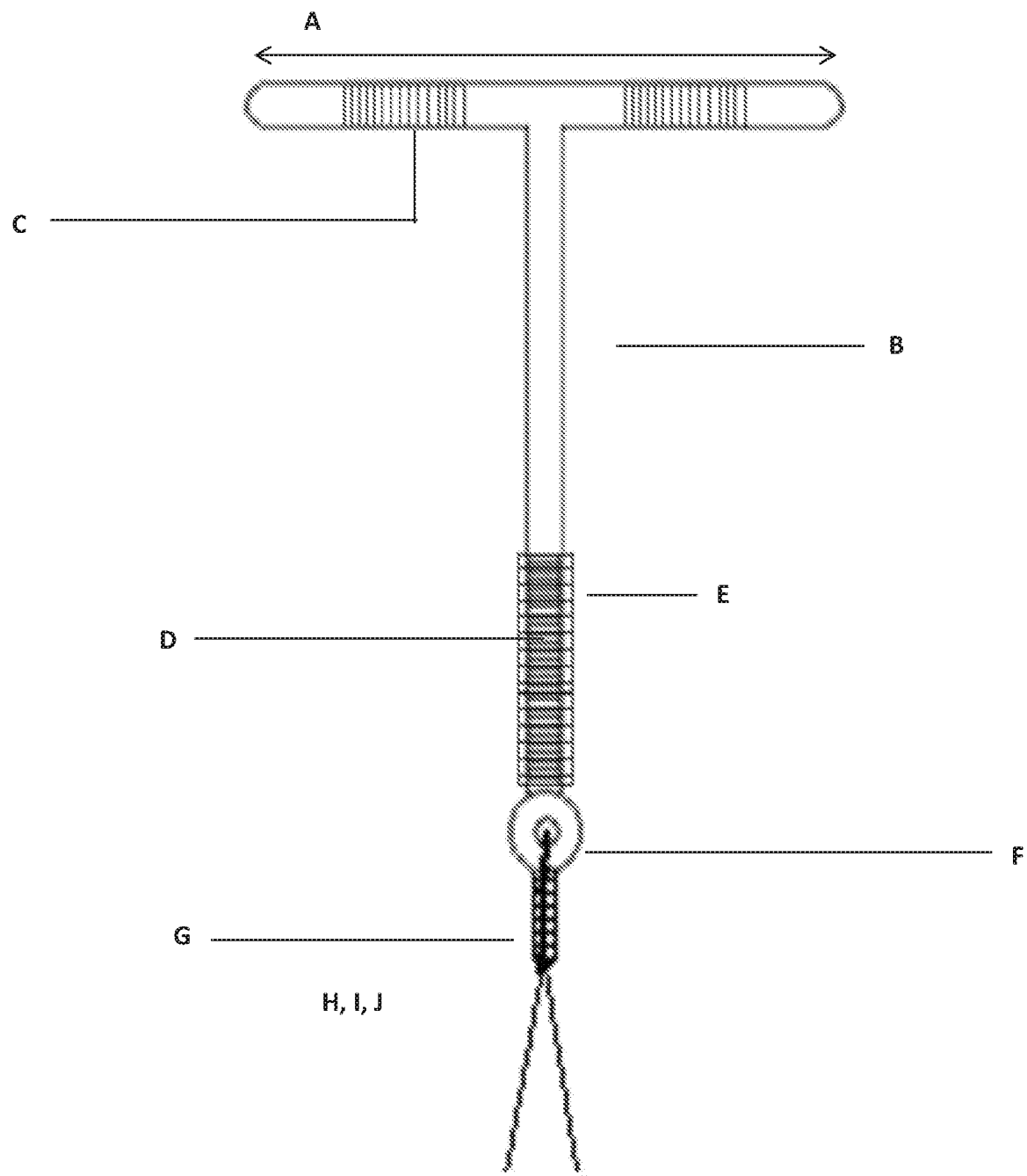

METHOD FOR REDUCING THE INCIDENCE AND PREVALENCE OF HUMAN PAPILLOMA VIRUS (HPV) AND FOR PROVIDING PROTECTION AGAINST SEXUALLY TRANSMITTED INFECTIONS

RELATED U.S. APPLICATION DATA

Continuation-in-part of application Ser. No. 15/100,900 filed on Jun. 1, 2016.

TECHNICAL FIELD

The invention is related to a method for reducing the incidence and prevalence of human papilloma virus (HPV), mainly types 16 and 18, and therefore to prevent the incidence of the uterine cervical cancer (CaCu); a method for modifying the cervical microbiome thus decreasing the inflammatory response; and a method for providing an increase in leukocytes which, consequently, causes an increase in local immunity in women infected with human papilloma virus and other sexually transmitted infections.

BACKGROUND

In the medical field, it has been reported that the use of the intrauterine device (UID) not only protects women from contraception, but it also provides protection against the cervical cancer and some sexually transmitted diseases (STD).

As it is known, the cervical cancer is the fourth leading cause of death in the women on the world. It is proved and established that the human papilloma virus (HPV) is the main cause of cervical cancer in women, particularly HPV types 16 and 18 types are commonly known as the highest risk viruses.

In this regard, according to one systematic review and meta-analysis published on 2017 [Cortessis K. Victoria, et. Al.; "Intrauterine device use and cervical cancer risk"; OBSTETRICS & GYNECOLOGY, Vol. 130, No. 6; 2017, p. 1226-1236.], there is a correlation between the occurrence probability to decrease the risk to develop cervical cancer, and the use of an intrauterine device; i.e., women users of an IUD showed a less incidence to develop cervical cancer in contrast with non-user women of IUD.

Said results are encouraging because the use of an IUD can be promoted as a preventive method against the cervical uterine cancer. Currently there are no effective treatments that allow the removal or eradicate of this type of cancer in advanced stages. Indeed, at the present time, the medical efforts are mainly directed at cancer prevention. One of the goals of the present invention is directed to this technical field.

According to a review published on 2007 [Diestro Tejada, M. D., et. al.; "Cancer de cuello uterino. Estado actual de las vacunas frente al virus del papiloma humano (VPH)"; Oncologia, 2007; 30 (2), p. 42-59] there are many factors involved in the development of cervical uterine cancer in women infected with HPV, some are intrinsic of the virus itself like the persistence of the infection; other are related to environmental factors as the type of the contraceptive method used, the lifestyle, the parity, if the women smokes or has suffered other co-infections as the *Chlamydia* infection, etc., which give us the idea that in order to prevent the cancer, we should act against a lot of involved factors.

Furthermore, another important environmental factor that should be considered is the cervicovaginal microbiota. The microbiota is a group of microorganisms that establish communication with human cells to maintain the homeostasis of the human body, for example, said microbiota can prevent the growth of pathogens. However, under some circumstances this balance is broken, and it can occur that some species that inhabit a specific niche is altered such that can lead to the development of pathologies like cancer.

An article summarized and published on 2018 [Madrid-Marina, Vicente, Torres Poveda Kirvisx; "La importancia de la microbiota cervicovaginal en cancer cervicouterino"; Mens. Bioquim. 42(2018) 57-63], the cervicovaginal microbiota (see Table 1) found in: a) women diagnosed without any cervical injury and HPV-negative; b) women diagnosed without cervical injury and HPV-positive; c) women diagnosed with cervical squamous intraepithelial lesions and d) women diagnosed with cervical uterine cancer.

TABLE 1

Cervicovaginal microbiota found in women with four different diagnostics according to [Vicente Madrid Marina, 2018].
CERVICOVAGINAL MICROBIOTA

| | |
|---|---|
| a) | *L. iners, L. crispatus, L. gasseri, L. jensenii Streptococcus agalactiae, Gardnerella vaginalis, Prevotella Sneathia* |
| b) | *L. iners, L. crispatus, L. gasseri, Gardnerella vaginalis, Pseudomonas oleovorans, Fusobacterium* spp |
| c) | *Sneathia* spp., *Fusobacterium* spp., *Atopobium vaginae, Megasphaera elsdenii, Shuttleworthia satelles, L. Crispatus, L. iners, Gardnerella vaginalis* |
| d) | *Fusobacterium necrophorum, Fusobacteria* spp., *Sneathia* spp., *Shuttleworthia* spp., *Streptoccoccus agalactiae* |

As can be seen in table 1, the composition of the microbiota of a healthy woman is different from the composition of a woman diagnosed with cancer. Likewise, the modification of the microbiota is related to the presence of intraepithelial lesion secondary to HPV.

In this regard, it is also disclosed in [Curty, GISLAINE, S. de Carvalho, PEDRO, and A. Soares, Marcelo; "The role of the cervicovaginal microbiome on the genesis and as a biomarker of premalignant cervical intraepithelial neoplasia and invasive cervical cancer"; International Journal of Molecular Sciences; 2020, 21, 222] that the microbiota plays an important role to control viral infections either a direct mechanism "or through of an indirect mechanism, by immune response inhibition or chronic inflammation".

In this sense, according to the composition of the microbiota, it can produce lactic acid and hydrogen peroxide which according to this article "have a protective effect against viral and bacterial infections".

Furthermore, the article discloses that recently were proposed two different mechanisms through how the microbiota contributes to the cancer associated with a viral infection. In the first mechanism suggested, the microbiota is affecting in a direct way the viral infectivity through "generation of bioproducts that could be able to module virus-host interactions". The second mechanism suggests that "bacteria-host interactions affect the host gene expression and this modulation on its turn affects viral production and could promote the tumorigenesis associated with viral infection".

Regarding the effect of copper present in the intrauterine devices and its relationship with viral infections, it has been disclosed in [Madrid-Marina, Vicente, Torres Poveda Kirvisx; "La importancia de la microbiota cervicovaginal en càncer cervicouterino"; Mens. Bioquim. 42(2018) 57-63] and [Gui L I U, M P H, et. al.; "HIV-positive women have higher risk of HPV infection, precancerous lesions, and cervical cancer: A systematic review and meta-analysis"; AIDS, Publish Ahead of Print, 2018] that one of the proposed mechanisms is related to the modification of the chemical environment produced by the presence of copper, which has a bactericidal, bacteriostatic, fungicidal and virucidal effect, thus increasing the clearance or elimination of the HPV viral load present, which would decrease the progression to a low-grade squamous intraepithelial lesion, to a high-grade squamous intraepithelial lesion, and its likely reversal.

Furthermore, according to the disclosed in the prior art, particularly in [Curty, GISLAINE, S. de Carvalho, PEDRO, and A. Soares, Marcelo; "The role of the cervicovaginal microbiome on the genesis and as a biomarker of premalignant cervical intraepithelial neoplasia and invasive cervical cancer"; International Journal of Molecular Sciences; 2020, 21, 222], it is explained that the presence of HPV alone is not sufficient for the development of CaCu, it is the secondary inflammatory response developed by its persistence that allows the progression to premalignant lesions mentioned above. In this regard, the modification of the environment and the cervicovaginal microbiota immunomodulates the persistence of HPV viral infection.

It is important to note that the development of intrauterine devices dates from the last century, and since then to date, their designs and the materials used for their manufacture have been improved so that their use is no longer limited exclusively to contraception.

Regarding the historical development of the devices, it is important to mention that, as disclosed in the prior art, with the discovery of the copper as a spermicide, the size of the devices was reduced and, consequently, the bleeding that is caused by the use of these ones. This confirms that both the dimensions of the intrauterine device and the copper concentration used on said device are important features.

All intrauterine devices disclosed in the prior art have the dimensions necessary to be placed and fixed inside the uterus of a woman.

On the other hand, there are also disclosed several intrauterine devices that in addition to containing copper in their design also comprise an active agent. Depending on the type of compound used, said intrauterine devices will reinforce contraception or help to control bleeding or even they can be used to treat some local infections such as *Chlamydia*, gonorrhea, and the like as it is disclosed in the international patent application WO200775086.

In spite of the aforementioned efforts, there is still a need in the art for uterine cervical devices that provides benefits against the human papillomavirus and the diseases derived thereof while providing, at the same time, benefits as contraceptive.

BRIEF DESCRIPTION

It is remarkable that the present invention is related to the specific use of the uterine cervical device granted in U.S. Pat. No. 10,702,470 and published in US 2016/0296468 (2016), said device only comprising copper and having the necessary dimensions allowing it to be placed and fixed between the cervix and the uterus of the woman.

In said publication, it is disclosed that said uterine cervical device is distinguished over prior art, among other reasons, due to the increased amount of copper used, wherein the concentration of the copper is between 380 $mm^2$ and 524 $mm^2$, preferably between 418 $mm^2$ and 524 $mm^2$; the presence of a copper filament in different shapes, such as Solomon Bar, Celtic Knot, Bracelet (H,I,J); a T-shaped frame formed of inert plastic material having between 15 and 23 weight percent radiopaque material, wherein the radiopaque material is a combination of barium sulfate and titanium oxide, and the presence of a sphere measuring 3.1 mm in diameter made of plastic and/or copper disposed at the end of a vertical arm of the device. In view of the above-mentioned, the present invention provides a method for reducing the incidence and prevalence of the human papillomavirus, mainly types 16 and 18, thus preventing the development of uterine cervical cancer in women.

In one embodiment of the invention, the invention also provides a method for modifying the cervical microbiota thus decreasing both the local inflammatory response measured with cytokines, without being bound by any theory, it is considered that cytokines involved may be, for instance, CD4 and CCR5 cytokines, and the progression of precancerous lesions in the cervix related to the human papilloma virus including the high-risk and the low-risk viruses, mainly the HPV types 16 and 18.

In an additional aspect, the invention further provides a method for an increase in leukocytes which, consequently, causes an increase in local immunity. Said increase of immunity provides protection for other sexually transmitted infections in women as *chlamydia* infection or gonococcal infection.

The scheme that marks carcinogenesis associated with damage to cellular DNA with the progression to premalignant lesions, associated with the inflammatory response, the infection by oncogenic viruses such as HPV 16 and HPV 18, as well as the modification of the immunological response is a highly synthesized scheme of the mechanisms of action of infection in the development of cervical cancer. In this sense, without being bound by any theory, the inventors of the invention consider the uterine cervical device used in the methods and their embodiments claimed in the present invention modifies the biochemical environment, reducing the presence or viral load of HPV, with a decrease in the inflammatory response, an increase in the local immune response by modifying the microbiota, and therefore migration to premalignant injury or malignant.

As should be evident for a skilled person, there are different mechanisms known in the art intended to explain the effect of copper over viral infections like VPH, and microbiota. Furthermore, it goes beyond the scope of this invention explaining such mechanisms. The purpose of this invention is disclosed in the different embodiments mentioned in previous lines.

BRIEF DESCRIPTION OF FIGURES

The FIG. 1 discloses a frontal view of a uterine cervical device used in the present invention comprising a plastic T-shaped frame with a horizontal arm (A), a vertical post (B) and at its lower end an sphere (F).

As it is shown, there is rolled up on each side of the horizontal arm a strand of copper (C); there are also rolled up two superimposed filament layers of copper (D) on the vertical arm wherein the coils of these filaments are spaced between them (E).

The FIGURE also shows that there are placed ends of a length of coiled copper within the sphere (G); said length can have different shapes as a Solomon Bar (H), Celtic Knot (I) or Bracelet (J).

DETAILED DESCRIPTION

Any person skilled in the art must understand all technical terms described herein. However, certain terms are defined in order to clarify the invention.

Therapeutic effect.—refers to a therapeutic and/or prophylactic benefit wherein the prophylactic benefit encompass the delay or the elimination of a disease or condition like the incidence of the human papilloma virus.

Treatment.—refers to the treatment of a disease or condition in a human, particularly in women and includes: the prevention (when the disease or condition is not yet suffered); the inhibition and the relief (once the woman is already infected with the disease or is suffering certain condition) which involves the detention of the development of the disease and/or condition, and the regression of the disease and/or condition relieving the suffered symptoms respectively.

Approximately or about—all measurable technical features like sizes, parameters, concentrations are not neither do need to be exact, i.e., these measurable technical features are disclosed as ranges which already includes the allowable tolerance. Hence, the use of the term "approximately" or "about" provides an additional determined range regarding the numeric value to which it is being applied. Said additional range provided by the term is approximately +10%. By way of example, but not in a limitative manner, if it reads "approximately 40 cm", the exact range which it describes and/or claims is between 36 to 44 cm.

Leukocytes—also called as a white blood cell, refers to those components present in the human body that defend it against all kind of diseases. They are divided into granular and agranular leukocytes, wherein the first group comprises the neutrophils, eosinophils, and basophils, and the second group comprises monocytes and lymphocytes.

Cytokines.—are proteins or glycoproteins produced by different cell types that act as regulators of immune and inflammatory responses.

Cervicovaginal microbiota.—refers to a dynamic group of microorganisms which can modulate the local immune response in the cervix and it can be classified into five groups according to [CURTY, Gislaine, et. al.; "The Role of the Cervicovaginal Microbiome on the Genesis and as a Biomarker of Premalignant Cervical Intraepithelial Neoplasia and Invasive Cervical Cancer"; Int. J. Mol. Sci. (2020), 21, 222, p. 5 of 24]; i.e., includes all community state types (CSTs) stated as CSTs I, II, III, IV and V according to dominant bacteria. For instance, *Lactobacillus crispatus, L. gasseri, L. iners,* and *L. jensenii* are the dominant species of CSTs I, II, III and V; meanwhile, the CST IV shows an increase of anaerobic species like *Gardnerella, Megasphera, Atopobium,* and *Prevotella*. A lot of environmental factors, for instance, sexual activity, the use of oral contraceptive or others, stress, etc., can change the composition of microbiota. Unless expressly stated otherwise, whenever we refer to cervicovaginal microbioma, it should be considered that it is formed by a lot of microorganisms already disclosed in the art.

The invention provides a method for reducing the incidence and prevalence of the human papillomavirus in women, mainly types 16 and 18, thus preventing the development of uterine cervical cancer in women and comprises the following steps:

1. Providing a uterine cervical device comprising copper between approximately 380 mm$^2$ to approximately 524 mm$^2$, preferably approximately 418 mm$^2$ to approximately 524 mm$^2$, distributed on a T-shaped frame having a horizontal arm having a length of between about 17.8 millimeters and about 32.2 millimeters, said T-shaped frame having a vertical post extending from the horizontal arm, the vertical post having a length of between about 25.8 millimeters and about 36.2 millimeters and a diameter of about 1.7 millimeters, the horizontal arm having portions on opposite sides of the vertical post and a sphere affixed to the vertical post; said T-shaped frame made of inert plastic like polyethylene, propylene, polyester or silicone elastomer.
2. Inserting said uterine cervical device inside of the female reproductive system, particularly in the lower part of the uterine cavity and endocervix where the human papillomavirus is incubated.
3. The device must be maintained in position up to approximately 5 years.

In an embodiment of the invention, the inserting step 2) is performed manually and without the use of any specific device for the insertion. That is, devices such as speculum, tenaculum, uterine sound, ring clips, scissors, usually used in the art are also used in said inserting step 2).

In a preferred embodiment of the invention, the uterine cervical device being used in the present method corresponds to that claimed and granted in the U.S. patent application Ser. No. 15/100,900, U.S. Pat. No. 10,702,470 which comprises:

A T-shaped frame formed of inert plastic material having between 15 and 23 weight percent radiopaque material, the radiopaque material being a combination of barium sulfate and titanium oxide, said T-shaped frame having a horizontal arm having a length of between 17.8 millimeters and 32.2 millimeters, said T-shaped frame having a vertical post extending from the horizontal arm, the vertical post having a length of between 25.8 millimeters and 36.2 millimeters and a diameter of 1.7 millimeters, the horizontal arm having portions on opposite sides of the vertical post;

a sphere affixed to the vertical post, said sphere being formed of inert plastic or copper, said sphere having a diameter of 3.1 millimeters;

a strand of copper wound on each of the portions of the horizontal arm, said strand of copper having a diameter of between 0.25 and 0.26 millimeters and having a total area of copper of between 35.8 and 36.2 square millimeters;

a pair of copper filaments wound on the vertical post, each of said pair of copper filaments having a diameter of 0.25 and 0.26 millimeters and a total area of copper of 100 square millimeters, the pair of copper filaments extending for a distance of between 20 and 25 millimeters;

a length of a copper filament having an area of between 146 and 250 square millimeters wound in a shape of a Soloman bar or a Celtic knot or a bracelet, wherein said length of the copper filament being positioned distal said sphere on said T-shaped frame, said sphere positioned between the vertical post and said length of the copper filament; and a low-density polyethylene thread having a length of 20 centimeters and a diameter of between 0.20 and 0.30 millimeters, said low-density polyethylene thread being affixed to said T-shaped frame and positioned inside said length of copper filament, a total amount of copper of said strand of copper and said pair of copper filaments and said length of copper filaments being between approximately 380 mm$^2$ to approximately 524 mm$^2$, preferably between approximately 418 and 524 square millimeters.

In the most preferred embodiment of the invention, the used uterine cervical device comprises 418 mm$^2$ of copper distributed on a T-shaped frame.

According to the method of the invention, the uterine cervical device may be maintained in position up to approximately 5 years, and more preferably up to approximately 3 years.

In one embodiment of the invention, the method as it is claimed also comprises the change of the uterine cervical device between approximately 3 to approximately 5 years after being inserted.

In other embodiment of the invention, the method disclosed above is also novel and inventive because it prevents the development of uterine cervical cancer showing a therapeutic effect because within the area of the sphere affixed to the vertical post are located the ends of a length of 99.9% pure copper winding with a length of approximately 150 to approximately 300 mm, and approximately 146 to approximately 250 mm² placed on the uterine cervical canal right opposite the folds or cavities of the cervix; i.e, the structure of the uterine cervical device of the invention allows to be placed within the uterus and the cervix of the woman where lesions caused by the human papilloma virus, mainly types 16 and 18, can develop into cancer.

According to the known measurements of cavimetries in women, the uterine cervical device used in the method of the present invention, advantageously, has the necessary dimensions so that it has contact not only with the uterus but also with the cervix of said population. Direct contact with the cervix is important, because as previously stated, it is in this area where HPV lodges and can become cancer.

Another embodiment of the invention is that the method disclosed above permits treatment of the uterine cervical cancer developed in women by allowing the involution of premalignant and malignant lesions through the decreasing of the local inflammatory response and the modification of the local microbiota.

Other embodiment of the invention is a method modifying the cervical microbiota of the women thus reducing the inflammatory response measured with cytokines and the progression of precancerous lesions in the cervix related to the human papilloma virus including the high-risk and the low-risk viruses; mainly the HPV types 16 and 18. This method comprises inserting the uterine cervical device disclosed previously into the female reproductive system, specifically in the lower part of the uterine cavity and endocervix. Said device must be maintained in position up to approximately 5 years, preferably up to three years.

In an additional aspect, one method of the invention further provides an increase in leukocytes which, consequently, causes an increase in local immunity.

The increased local immunity provides protection for other sexually transmitted infections in women as *chlamydia* infection or gonococcal infection.

Said method permitting an increment on the leukocytes comprises inserting the uterine cervical device disclosed previously into the female reproductive system, specifically in the lower part of the uterine cavity and endocervix. Said device must be maintained in position up to approximately 5 years, preferably up to three years.

Experimental Studies

The uterine cervical device disclosed in the invention will be mainly tested in patients already infected with the human papilloma virus, mainly types 16 and 18, by inserting said device into the lower part of the uterine cavity and endocervix, to demonstrate the reduction in the incidence and prevalence of the human papillomavirus in women, mainly types 16 and 18, thus preventing the development of uterine cervical cancer in women.

Further, said device will be also tested to demonstrate that by inserting it into patients already suffering from uterine cervical cancer can be effectively treated such that involution of premalignant and malignant lesions can be expected thus leading to an improvement of the patient's life.

In another aspect, said device will be tested in patients already infected with the human papilloma virus, mainly types 16 and 18, to determine and evaluate the viral load and the inflammatory load within the uterine and cervix of the woman by measuring the cytokines, in particular cytokines CD4 and CC4, in three different moments. The first measurement will be made before inserting the uterine cervical device; the second one will be done six months after the uterine cervical device was inserted; and the third one will be performed twelve months after the uterine cervical was inserted. Variations in these time intervals may occur as should be evident for a skilled person.

Additionally, the device will be tested in patients already infected with the human papilloma virus, mainly types 16 and 18, when introducing the uterine cervical device to demonstrate the women's microbiome was modified after the device was introduced and placed inside their uterus and cervix.

In a further aspect, the therapeutic effect of the device will be tested in women not suffering from a VPH infection or a uterine cervical cancer to demonstrate the preventing effect of the method.

Finally, the embodiments of the invention which have been described do not attempt to limit the scope of the invention; rather simply illustrate some of the variations which are found comprised within the spirit of the invention and the scope of the same. As will be obvious to a person skilled in the art, the variations or amendments which do not depart from the spirit of the invention are found to lie within the scope thereof.

The invention claimed is:

1. A method for reducing the incidence and prevalence of the human papillomavirus types 16 and 18 in women, thus preventing the development of uterine cervical cancer in women, comprising the following steps:
   providing a uterine cervical device comprising copper having a surface area between approximately 380 mm2 to approximately 524 mm2, distributed on a T-shaped frame having a horizontal arm having a length of between about 17.8 millimeters and about 32.2 millimeters, said T-shaped frame having a vertical post extending from the horizontal arm, the vertical post having a length of between about 25.8 millimeters and about 36.2 millimeters and a diameter of about 1.7 millimeters, the horizontal arm having portions on opposite sides of the vertical post and a sphere affixed to the vertical post; said T-shaped frame made of at least one member of a group comprising: polyethylene, propylene, polyester and silicone elastomer;
   inserting said uterine cervical device in the lower part of the uterine cavity and endocervix,
   wherein the device is maintained in position up to approximately 5 years.

2. The method according to claim 1, wherein the uterine cervical device comprises a surface area of approximately 418 mm2 to approximately 524 mm2.

3. The method according to claim 1, wherein the uterine cervical device is maintained in position between approximately 3 years to approximately 5 years.

4. The method according to claim 1, wherein the insertion of the uterine cervical device is performed manually.

5. The method according to claim 1, further comprises the change of the uterine cervical device between approximately 3 to approximately 5 years after being inserted.

6. The method according to claim 1 wherein the uterine cervical device comprises:
- a T-shaped frame formed of inert plastic material having between 15 and 23 weight percent radiopaque material, the radiopaque material being a combination of barium sulfate and titanium oxide, said T-shaped frame having a horizontal arm having a length of between 17.8 millimeters and 32.2 millimeters, said T-shaped frame having a vertical post extending from the horizontal arm, the vertical post having a length of between 25.8 millimeters and 36.2 millimeters and a diameter of 1.7 millimeters, the horizontal arm having portions on opposite sides of the vertical post;
- a sphere affixed to the vertical post, said sphere being formed of inert plastic or copper, said sphere having a diameter of 3.1 millimeters;
- a strand of copper wound on each of the portions of the horizontal arm, said strand of copper having a diameter of between 0.25 and 0.26 millimeters and said strand of copper having a total area of copper of between 35.8 and 36.2 square millimeters;
- a pair of copper filaments wound on the vertical post, each of said pair of copper filaments having a diameter of 0.25 and 0.26 millimeters and each of said pair of copper filaments having a total area of copper of 100 square millimeters, the pair of copper filaments extending for a distance of between 20 and 25 millimeters;
- a length of a copper filament having an area of between 146 and 250 square millimeters wound in a shape of a Soloman bar or a Celtic knot or a bracelet, wherein said length of the copper filament being positioned distal said sphere on said T-shaped frame, said sphere positioned between the vertical post and said length of the copper filament; and
- a low-density polyethylene thread having a length of 20 centimeters and a diameter of between 0.20 and 0.30 millimeters, said low-density polyethylene thread being affixed to said T-shaped frame and positioned inside said length of copper filament, a total surface area of copper of said strand of copper and said pair of copper filaments and said length of copper filaments being between approximately 380 mm2 to approximately 524 mm2.

7. The method according to claim 1 to treat the uterine cervical cancer developed in women by allowing the involution of premalignant and malignant lesions.

8. A method to modify the cervical microbiota of the women comprising the following steps:
- providing a uterine cervical device comprising copper having a surface area between approximately 380 mm2 to approximately 524 mm2, distributed on a T-shaped frame having a horizontal arm having a length of between about 17.8 millimeters and about 32.2 millimeters, said T-shaped frame having a vertical post extending from the horizontal arm, the vertical post having a length of between about 25.8 millimeters and about 36.2 millimeters and a diameter of about 1.7 millimeters, the horizontal arm having portions on opposite sides of the vertical post and a sphere affixed to the vertical post; said T-shaped frame made of at least one member of a group comprising: polyethylene, propylene, polyester and silicone elastomer;
- inserting said uterine cervical device inside of the female reproductive system, particularly in the lower part of the uterine cavity and endocervix where the human papillomavirus is incubated,
wherein the device is maintained in position up to approximately 5 years.

9. The method according to claim 8, further decreasing the local inflammatory response.

10. The method according to claim 8, further reducing the progression of precancerous lesions in the cervix related to the human papilloma virus types 16 and 18.

11. The method according to claim 8, wherein the uterine cervical device comprises:
- a T-shaped frame formed of inert plastic material having between 15 and 23 weight percent radiopaque material, the radiopaque material being a combination of barium sulfate and titanium oxide, said T-shaped frame having a horizontal arm having a length of between 17.8 millimeters and 32.2 millimeters, said T-shaped frame having a vertical post extending from the horizontal arm, the vertical post having a length of between 25.8 millimeters and 36.2 millimeters and a diameter of 1.7 millimeters, the horizontal arm having portions on opposite sides of the vertical post;
- a sphere affixed to the vertical post, said sphere being formed of inert plastic or copper, said sphere having a diameter of 3.1 millimeters;
- a strand of copper wound on each of the portions of the horizontal arm, said strand of copper having a diameter of between 0.25 and 0.26 millimeters and said strand of copper having a total area of copper of between 35.8 and 36.2 square millimeters;
- a pair of copper filaments wound on the vertical post, each of said pair of copper filaments having a diameter of 0.25 and 0.26 millimeters and each of said pair of copper filaments having a total area of copper of 100 square millimeters, the pair of copper filaments extending for a distance of between 20 and 25 millimeters;
- a length of a copper filament having an area of between 146 and 250 square millimeters wound in a shape of a Soloman bar or a Celtic knot or a bracelet, wherein said length of the copper filament being positioned distal said sphere on said T-shaped frame, said sphere positioned between the vertical post and said length of the copper filament; and
- a low-density polyethylene thread having a length of 20 centimeters and a diameter of between 0.20 and 0.30 millimeters, said low-density polyethylene thread being affixed to said T-shaped frame and positioned inside said length of copper filament, a total surface area of copper of said strand of copper and said pair of copper filaments and said length of copper filaments being between approximately 380 mm2 to approximately 524 mm2.

12. A method to provide an increment in leukocytes in women comprising the following steps:
- providing a uterine cervical device comprising copper having a surface area between approximately 380 mm2 to approximately 524 mm2, distributed on a T-shaped frame having a horizontal arm having a length of between about 17.8 millimeters and about 32.2 millimeters, said T-shaped frame having a vertical post extending from the horizontal arm, the vertical post having a length of between about 25.8 millimeters and about 36.2 millimeters and a diameter of about 1.7 millimeters, the horizontal arm having portions on opposite sides of the vertical post and a sphere affixed to the vertical post; said T-shaped frame made of at least one member of a group comprising: polyethylene, propylene, polyester and silicone elastomer;

inserting said uterine cervical device inside of the lower part of the uterine cavity and endocervix, wherein the device is maintained in position up to approximately 5 years.

13. The method according to claim 12, local immunity in women.

14. The method according to claim 13, further protecting against sexually transmitted infections in women.

15. The method according to claim 14, wherein sexually transmitted infections are selected from *chlamydia* and gonococcal infections.

16. The method according to claim 12, wherein the uterine cervical device comprises:

a T-shaped frame formed of inert plastic material having between 15 and 23 weight percent radiopaque material, the radiopaque material being a combination of barium sulfate and titanium oxide, said T-shaped frame having a horizontal arm having a length of between 17.8 millimeters and 32.2 millimeters, said T-shaped frame having a vertical post extending from the horizontal arm, the vertical post having a length of between 25.8 millimeters and 36.2 millimeters and a diameter of 1.7 millimeters, the horizontal arm having portions on opposite sides of the vertical post;

a sphere affixed to the vertical post, said sphere being formed of inert plastic or copper, said sphere having a diameter of 3.1 millimeters;

a strand of copper wound on each of the portions of the horizontal arm, said strand of copper having a diameter of between 0.25 and 0.26 millimeters and said strand of copper having a total area of copper of between 35.8 and 36.2 square millimeters;

a pair of copper filaments wound on the vertical post, each of said pair of copper filaments having a diameter of 0.25 and 0.26 millimeters and each of said pair of copper filaments having a total area of copper of 100 square millimeters, the pair of copper filaments extending for a distance of between 20 and 25 millimeters;

a length of a copper filament having an area of between 146 and 250 square millimeters wound in a shape of a Soloman bar or a Celtic knot or a bracelet, wherein said length of the copper filament being positioned distal said sphere on said T-shaped frame, said sphere positioned between the vertical post and said length of the copper filament; and a low-density polyethylene thread having a length of 20 centimeters and a diameter of between 0.20 and 0.30 millimeters, said low-density polyethylene thread being affixed to said T-shaped frame and positioned inside said length of copper filament, a total surface area of copper of said strand of copper and said pair of copper filaments and said length of copper filaments being between approximately 380 mm2 to approximately 524 mm2.

17. The method according to claim 6, wherein the uterine cervical device comprises a total surface area of copper of said strand of copper and said pair of copper filament and said length of copper filaments between approximately 418 mm2 to approximately 524 mm2.

18. The method according to claim 11, wherein the uterine cervical device comprises a total surface area of copper of said strand of copper and said pair of copper filament and said length of copper filaments between approximately 418 mm2 to approximately 524 mm2.

19. The method according to claim 16, wherein the uterine cervical device comprises a total surface area of copper of said strand of copper and said pair of copper filament and said length of copper filaments between approximately 418 mm2 to approximately 524 mm2.

* * * * *